United States Patent [19]
Castro

[11] Patent Number: 6,030,843
[45] Date of Patent: Feb. 29, 2000

[54] SITE REACTIVITY PROBES FOR THE ENVIRONMENT

[75] Inventor: Charles E. Castro, Laguna Beach, Calif.

[73] Assignee: The Regents of the University of California, Oakland, Calif.

[21] Appl. No.: 08/692,832

[22] Filed: Jul. 31, 1996

[51] Int. Cl.$^7$ ........................... G01N 24/00; C07C 51/00; C07C 53/08; C07C 53/16
[52] U.S. Cl. .............................. 436/173; 422/61; 562/840
[58] Field of Search ............................ 562/840; 436/173; 422/61

[56] References Cited

FOREIGN PATENT DOCUMENTS 5-163273  6/1993  Japan .

OTHER PUBLICATIONS

S.N. Jacobson et al. *Appl. Environ. Microbiol.* 1981, 42, 1062–1066.
K.G. Au et al. *Bioorg. Chem.* 1984, 12, 197–205.
A. Krause et al. *J. Agric. Food Chem.* 1985, 33, 584–589.
M. Urbanek et al. *Lett. Appl. Microbiol.* 1989, 9, 191–194.
A. Konopka *Appl. Microbiol. Biotechnol.* 1994, 42, 440–445.
R.R. Fulthorpe et al. *Appl. Environ. Microbiol.* 1996, 62, 1159–1166.
M. Horie et al. *Chem. Pharm. Bull.* 1978, 26, 1009–1014.
V.N. Kerr et al. *J. Labelled Compd. Radiopharm.* 1978, 15, 503–509.
B.D. Andresen et al. *J. Labelled Compd. Radiopharm.* 1978, 15, 731–738.
D.C. Billington et al. *J. Labelled Compd. Radiopharm.* 1981, 18, 1773–1784.
G. Zomer et al. *Steroids* 1984, 44, 283–292.
Aldrich Catalog 1988, pp. 320 & 748.
J.M. Harrison *J. Labelled Compd. Radiopharm.* 1991, 29, 1175–1180.
R. M. Jarret et al. *Microchem. J.* 1993, 47, 187–192.
G. Grue–Sørensen et al. *J. Am. Chem. Soc.* 1994, 116, 6195–6200.
R.E. Carhart et al. *Org. Magn. Resonance* 1971, 3, 139–141.
B. Tecle et al. *Chem. Res. Toxicol.* 1989, 2, 429–435.
H. Johansen *Z. Phys Chem.* 1964, 227, 305–328.
J.I. DeGraw et al. *J. Labelled Compd. Radiopharm.* 1982, 19, 945–952.
R.E. Carhart et al. *Chem. Abstr.* 1971, 75, 28019k.
M. Igbal et al. *J. Labelled Compd. Radiopharm.* 1985, 22, 807–817.
B. Nitsche et al. *J. Labelled Compd. Radiopharm.* 1987, 24, 623–630.
H. Cho et al. *J. Labelled Compd. Radiopharm.* 1992, 31, 589–594.
J.R. Pribish *J. Labelled Compound Radiopharm.* 1995, 36, 225–233.
J.H. Slater et al. *Philos. Trans. R. Soc. London Ser. B* 1982, 297, 129–15 .

S.J. Weiner et al. *Magn. Reson. Chem.* 1994, 32, 122–127.
K.H. Popp *GWF, Gas–Wasserfach: Wasser/Abwasser* 1985, 126, 286–292.
C.E. Castro et al. *Environ. Toxicol. Chem.* 1992, 11, 749–755.
U. Heinze et al. *Appl. Microbiol. Biotechnol.* 1993, 40, 158–164.
C.E. Castro *Environ. Toxicol. Chem.* 1993, 12, 1609–1618.
R.B. Yeardley, Jr. et al. *Environ. Toxicol. Chem.* 1995, 14, 1189–1194.
Ahmed, et al, Bioactivation of Foreign Compounds, Anders, M.W. Ed.; Academic:New York, Chapter 17 (Nitriles), pp. 485–518.
Castro, et al, "Biodehalogenation: Oxidative and Hydrolytic Pathways in the Transformations of Acetonitrile, Chloroacetonitrile, Chloroacetic Acid, and Chloroacetamide by *Methylosinus tri–chosporium* OB–3b," *Environmental Science & Technology*, 30(4):1180–1184, 1996.
Castro, et al, "Site Reactivity Probes: [1,2–$^{13}$C] Chloracetic Acid, a Reactivity Probe for Soil," *Environmental Science & Technology*, 29(8):2154–2156, 1995.
Firmin, J.L. and Gray, D.O., "The Biochemical Pathway for the Breakdown of Methyl Cyamide (Acetonitrile) in Bacteria," *Biochem. Journal*, 158:223–229, 1976.
Green, J. and Dalton, H., "Substrate Specificity of Soluble Methane Monooxygenase: Mechanistic Implications," *Journal of Biological Chemistry*, 264(30):17698–17703, Oct. 1989.
Krauskopf, K.B. and Rollefson, G.K., "The Photochemical Reaction Between Chlorine and Formaldehyde. The Preparation of Formyl Chloride," *Journal of Am. Chem. Soc.*, 56:2542–2548, Jul. 1934.
Nishiyama, et al, "Cloning and Characterization of Genes Responsible for Metabolism of Nitrile Compounds from *Pseudomonas chlororaphis* B23," *Journal of Bacteriology*, 173(8):2465–2472, Apr. 1991.
Castro, et al., "C–NMR Reactivity Probes for the Environment," *Environ. Sci. Technol.*, 30:1185–1191, 1996.

*Primary Examiner*—Arlen Soderquist
*Attorney, Agent, or Firm*—Hana Verny

[57] ABSTRACT

The 136 labeled compounds chloroacetic acid (CA), chloroacetamide (CAM), and chloroactonitrile (CCN), have been synthesized, and provide the site reactivity probes (SRP) of the present disclosure. The reactivity of diverse environmental sites and samples, including activated sludge, dump sites, coastal marne water, soil, and lake sediments, have been assessed for site reactivity using the disclosed probes, and provide a useful and accurate index of the sites transformation potential and environmental profile. Methods of using these probes in the assessment of a sample from a desired environment are also disclosed. Application in health, remediation, and environmental profiling of a region may be provided with the various site reactivity probes described. Particular methods for assessing the effectiveness of remediation efforts and in gauging the effects of treatments to an environmental site are further particular applications of the technology disclosed herein.

18 Claims, 3 Drawing Sheets

SITE REACTIVITY PROBES FOR THE ENVIRONMENT

FIELD OF THE INVENTION

The field of the present invention relates to chemical probes and uses thereof in assessing reactivity of an environmental region.

BACKGROUND OF THE INVENTION

The chemical transformation wrought by the terrestrial and aquatic environments shape and foster the generation of life in all forms and maintain a balance in the ecosystem that nurtures it. As a part of the great cycle of transformations that occur in soil, the sea, and lake constitute a myriad of reactions in the environment that may be involved in the transformation of xenobiotics. Methods and tools for assessing such reactivity in the environment have not been heretofore available.

Assessing the reactivity of any given segment to the environment for chemical or biochemical conversion would be a valuable asset for predicting the rate and nature of the processes by which xenobiotics may be transformed in the soil-water sphere. A knowledge of this reactivity could also be used as a guide for choosing pesticides that may be environmentally tolerable or rapidly degraded at a given site. Moreover, reactivity probes should be a convenient means of assessing the effectiveness of remediation efforts. At this time, however, there is no methodology in place that will monitor reactivity directly. Although pH and redox potential can be monitored, they do not necessarily relate to a given site's capacity for transformation.

The basic chemical or biochemical processes a substance may undergo are oxidation, reduction, or substitution. Soil microbes are capable of transforming alkyl halides by all of these processes. The potential transformation of substances by exogenous enzymes and metal or metal ion mediated oxidation or reduction may also be expected. Substances that are useful for monitoring these events in the environment however are not available. Ideally, such a substance or testing protocol would provide accurate readings of these events in a terrestrial or water/aquatic sample with little sample work up and preparation, and require only small amounts of the reactivity detecting reagent. An environmental probe/reagent of this nature, and the diagnostic products derived from it should be easily analyzed and quantifiable.

SUMMARY OF THE INVENTION

The present invention provides novel environmental probes and uses thereof for the assessment of reactivity of an environmental region. Reactivity as used in the description of the present invention is defined as the capacity of a region to support oxidation, reduction, and substitution reactions as measured through use of the environmental probes described herein. The inclusion of these probes or any one of the probes in a reaction mixture that includes a test sample from the environment of interest provides a technique for assessing these processes, and is correlated with the relative potential for transformation in the region from which the sample was obtained.

The chemical reactivity probes of the invention comprise a structure:

13X13CHR$_1$-Y wherein X is a halogen, such as Cl, F, Br, or I, and wherein Y comprises an adjacent 13C-labeled carbon moiety. Y may be further defined as 13CN, 13CONR2, 13CO2H or salts thereof, 13CH2OH, 13CCHO, 13CH2SO3H or salts theof, 13C-R2,R3,R4,13C=O(R2) or 13C=S(R2), wherein R2, R3 or R4 comprises alkoxy, amino, substituted amino, aryloxy, H, alkyl, thioalkoxy, thiyl, arylthio, alkynyl, aryl, substituted aryl, cyclic, polycyclic, heterocyclic, or substituted heterocyclic moiety. R1 is further defined as H, halogen, acyl, aryl, alkynyl, or any tertiary carbon atom.

The probes in particular embodiments are further defined as water soluble. The chemical substitution reaction is further defined as hydrolysis in particular aspects of the invention.

The present invention in another aspect provides a method for assessing potential for oxidation, reduction, or substitution reactivity of a test environment. These environments may be of soil or water, both fresh and marine water environments. In one aspect, the method comprises exposing a sample from the test environment to the reactivity probe as described above. In particular aspects, the probe is 1,2-13C-chloroacetic acid, 1,2-13C-chloroacetamide, and 1,2-13C-chloroacetonitrile. In a particular aspect, the method may be further defined as comprising the steps of exposing an amount of the reactivity probe to a sample from a test environment to provide a reaction mixture, incubating the reaction mixture for a period of time sufficient to allow oxidation, reduction or substitution, assessing distribution of oxidative, reduction and substitution products and unreacted probe by NMR in the reaction mixture, and assessing the amount of probe and the amount of oxidative, reduction, and substitution products,wherein the relative percent conversion of the probe to products provides an assessment of the reactivity of the test environment.

In some aspects, the period of time that the probe will be incubated with the sample is about 1 to about 2 weeks. In some aspects, the period of incubation is about 2 weeks. The amount of the probe to be employed in the method will vary with the amount of the sample from the test environment being examined, as well as with the form of the test sample (i.e. liquid vs. solid sample). By way of example, the amount of probe in the reaction mixture is 10–9 moles/gram sample. In further defined aspects, the amount of sample to be used with a particular assessment of an environmental region is described as a molar amount. For example, where a solid sample (i.e., soil) is being tested, then one would preferably use a 1:2 sample to water suspension together with about 1 μl of a 10–3 M solution of the probe. However, other sample to water mixtures and molar amounts of probe respective thereto may also be employed without departing from the spirit and scope of the invention.

The methods of the invention have many different applications, including the identification of an environmental region as having a high transformation potential. A high transformation potential for purposes of the present invention is described as the potential of an area to support oxidation, reduction or substitution reactions. Such a region would be predicted to have a high capacity for neutralizing environmental challenges, such as challenge by a particular pesticide treatment or as a potential site for the disposal of waste products. The methods may also be used to asses the effectiveness of remediation efforts in a particular environmental region that had been polluted.

A high transformation potential of the region is defined as a region from which a test sample demonstrates an about 50% to about 100% conversion, preferably about 70% to about 100%, most preferably about 80% to about 100%, of the probe to products of oxidation, substitution, or reduction. A low transformation potential is defined as a region from which a test sample demonstrates an about 0% to about 10%, conversion of the probe to products.

The environmental regions that may be assessed using the preparations and methods of the invention include but are not limited to, marine sediment or water, fresh water sediment or water, soils, land fill, sewage, soil and biological products, such as seed, grain, and plants. The invention may also be used to asses degradation and/or quality control of stored materials, such as the aforementioned soil or grain/agricultural products.

The invention also provides a kit that may be used to provide the various assessments/quality control/remediation assessment protocols as outlined herein. These kits include as an clement the reactivity probes as described above, and optionally a container means for placing a test sample from the test environment or product store under scrutiny.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Materials. Chloroacetic acid-1,2-$^{13}$C was prepared by the slow decomposition of sulfuryl chloride in acetic acid-1,2-$^{13}$C in the presence of phosphorous pentachloride. The amide was prepared by aminolysis of the methyl ester. The latter was obtained by converting the chloroacid 25 first to chloroacetyl chloride and then to - the ester. Chloroacetonitrile 1,2-$^{13}$C was prepared by dehydrating the amide with phosphorus pentoxide. The details of these syntheses have recently been reported (9,10). Acetonitrile 1,2$^{13}$C and potassium cyanide $^{13}$C were purchased from Cambridge Isotopes, Andover, Ma. They were used without purification. The $^{13}$C nmr of both substances accorded with the literature.

[1,2$^{13}$C] Chloroacetic Acid. Into a 10-ml. flask equipped with reflux condenser and CaCl$^2$ drying tube, 1.0 g of [1,2$^{13}$C] acetic acid (Sigma Chemical Co., St. Louis, Mo.) (0.016 mol). 1.4 ml of SO$_2$Cl$_2$ (0.017 mol), 5 mg of PCl$_8$ and one drop of acetic anhydride were placed. The mixture was brought to 80° C. and held at that temperature under slight reflux for 1 day. At this time, the $^{13}$CNMR analysis indicated that an equal amount of acetic acid and chloroacetic acid was present (~50% conversion). An additional 1.4 ml. of SO$_2$Cl$_2$ was added through the condenser, and the solution was heated to 80° C. for another day. At this time, $^{13}$CNMR of the mixture indicated a mix of 2:5:1 CH$_2$Cl:CH$_3$ or a 71% conversion to CA. A trace of Cl$_2$CH at 66 δ corresponding to dichloroacetic acid could be seen. At this point, the mixture was distilled. After bringing off unread SO$_2$Cl$_2$ at 60° C., the flask was warmed to 130° C. until no further distillate (unreacted acetic acid) was obtained. The product, [1,2-$^{13}$C] chloroacetic acid was distilled at 100° C./20 mm and crystallized. Weight was 1.0 g. Note: This substance is hydroscopic. A stock 1 M solution of CA in dimethylforamide (DMF) was prepared for testing the probe. CA does not react with the solvent, and solutions have been stable for 2 years.

[1,2$^{13}$C] Chloroacetamide (CAM). In a small flask equipped with reflux condensor and drying tube, 2.8 g of [1,2$^{13}$C] chloroacetic acid (0.030 mol) was refluxed with 3.5 ml. (0.050 mol) of thionyl chloride at 76° C. for 4 hours. At this time, the $^{13}$C-NMR analysis indicated a complete conversion to the acid chloride (ClCH$_2$, δ 49, d; COCl δ 167, d). At room temperature, the flask contents were stirred and treated with 3 ml of methanol in dropwise fashion over a period of 15 minutes. The mixture was warmed to 55° C. for 7 hours. The cooled mixture indicated a complete conversion to the methyl ester (ClCH$_2$, δ 41, d; CO$_2$Me, δ 168, d). The flask was cooled to 2° C., and with stirring 7.0 ml. of cooled concentratedammonium hydroxide was added over a 0.5-h period. The mixture was stirred for 1.5 hours at 0–2° C. The white amide precipitate was vacuum filtered and recrystallized from hot water, filtered, and air dried. The overall yield of chloroacetamide was 1.8 g (64%). The white needles had melting point of 118.5–119. $^{13}$C-NMR: ClCH$_2$, δ 42, d; CONH$_2$, δ 172, d. Note: the more direct reaction of the acid chloride with ammonium acetate in acetone (7) yielded only 31% of the amide.

[1,2$^{13}$C] Chloroacetonitrile (CCN). To a 25-ml. three-necked flask equipped with a good mechanical stirring, a small distillation head, and a receiver was added 1.3 g (0.014 mol) of [1,2$^{13}$C] chloroacetamide. The flask was brought to 130° C. and held there until all of the amide had melted. The receiver was immersed in an ice bath, and a slurry of 1.9 g of phosphorous pentoxide (0.014 mol) in 2 ml. of freshly distilled 1,2,4-trichlorobenzene was added all at once. With vigorous sting, the flask was brought to 140–150° C. for 0.5 hours and then rapidly to 175° C. for another 0.5 hour. The water white [1,2-$^{13}$c] chloroacetonitrile liquid, 0.4 g, was obtained in 37% yield. $^{13}$C-NMR: ClCH$_2$, δ 25, d; CN, δ 117, d.

The chemical shifts for products have been given elsewhere (5,6). The $^{13}$C—$^{13}$C coupling constants were ~2 Hz.

The main point these data establish is that soil, fresh water sediments, manne sediments, and sludge all have a high capacity for the transformation of xenobiotics. The complete oxidation of an three probes to bicarbonate in 2 weeks or less is not uncommon. Clearly this is a multistep process that likely entails the initial hydrolysis of the C—Cl bond. In many cases where the oxidation of CAM and CCN is observed, CA is also a major product. The general oxidation of CAM and CCN proceeds via an initial hydrolysis of the amide and nitrile moieties to CA followed by hydrolysis and oxidation of the later. CAM is both hydrolyzed and oxidized to bicarbonate by the 1 year old dump site soil, and repeated studies confirm this.

The CA probe is the simplest and gives the most direct assessment of reactivity. In terms of overall sensitivity, CA is more reactive than CAM or CCN. Based upon conversion by the four segments of the environment tested, the order of reactivity is CA>CAM>CCN. For example with LP-1 (Table 2), the percent conversion of the various probes at 2 weeks in anaerobic incubations is CA (100), CAM (60), and CCN(0). With LP-2, the conversion ratios are 100:50:0, and with d.soil (Table 1) they are 100:48:30. On the other hand, the CAM and CCN probes do allow a direct measure of amide and nitrire hydrolysis rates.

In interpreting the responses of CA, it is important to realize that products corresponding to hydrolysis, reduction, or oxidation may not be detected if they are more quickly converted to $CO_2$ than the initial reaction with CA occurs. This is very clear with activated sludge where in only 4 days (Table 4, line 1) a 50% conversion to bicarbonate occurred, but no intermediates were detected. The anaerobic incubation (line 3) slowed the overall oxidation, however, such that glycolic acid (hydrolysis product) was observed. In such cases, a reduction to acetic acid followed by oxidation (eq 4) may also be missed. This pathway may be expected in mixed aerobic-anaerobic environments (e.g., Table 3, line 7). An observation of $HCO_3^-$ from CA does indicate oxidative capacity at the tested site, but additional processes may be discerned by an anaerobic or partially anaerobic incubation.

Comparing the response of all three probes with each segment of the environment allows the latter to be ranked for general overall reactivity. As an approximation of aerobic transformation capacity, the percent conversion of each probe at a 2-week incubation was added. The ranking and sum of the percentage conversion (in parentheses) is as follows: AS (300)>SC-1 (250)>d.S (190–200)>LP-1 and LP-2 (150–160)>d.S-1 year-old (134)>LSW, MSW (0). Assuming SC-2 would completely mineralize CA in 2 weeks as it did CAM, it would rank with SC-1. Using CA alone as the probe, where mineral on if the major occurrence, the ranking would be LP-1, LP-2~AS>d.S (100)>SC-1, SC-2 (~60)>d.S-1 year old, LSW, MSW (0). (The LP-1 and LP-2 samples mineralize CA in less than 1 week.) The similarity in results with CAM and CCN with the fresh or 1 year old dump site soil suggest that the hydrolysis of the amide and nitrile moieties is a chemical rather than microbial conversion catalyzed by this soil.

In this work, the probe concentrations varied from ~100 to 200 ppm, yet in many cases they were mineralized in less than 2 weeks. A large diverse capacity for the transformation of xenobiotics may be detected to exist in the terrestrial environment. Moreover, $^{13}$C-NMR site reactivity probes can monitor the nature and assess the speed of these processes in a direct and simple way.

The probes can provide the basis for a reasonable approximation of the nature and rate of transformation of other substances.

The organism *Methylosinus trichosporium* OB-3b was grown at 30° C. on methane in a low copper medium in a 5-L New Brunswick BioFlow II fermentor. A fixed ratio of methane to air 1:4 at 250 mL/min and a stiring speed of 300 rpm were employed. Centrifuged cells were suspended in phosphate buffer (0.1 M, pH 7.4) and recentrifuged thrice before reaction (11). Cells grown in the absence of any copper did not show an enhanced rate of substrate metabolism.

Methods. All transformations with the OB-3b cell line were conducted with resting cells at a concentration of 0.1 g wet wt./mL in phosphate buffer, pH 7.4 in the manner previously described (8). Substrates were 10–3 M originally. As before, 125 ml Erlenmeyer flasks filled with air and 20 ml of cells were employed. The flasks were sealed with a serum capped stopcock. The total volume of each flask was ~160 ml. Approximately 0.5–1 ml samples were removed at the desired time for $^{13}$C nmr analysis. These samples were transferred to (5 mm id) stoppled nmr tubes. The cell suspension in the nmr tubes was immersed in boiling water for 1 min and the sample was held at 5° until the nmr acquisition could begin. One hundred pl of D20/ml of cell suspension was added for the lock.

NMR Analysis. The spectrum of naturally abundant (1.1%) $^{13}$C compounds at 0.001M is invisible under our conditions because of the low sensitivity of the $^{13}$C nucleus to nmr. At higher concentrations, however, spectra can be observed. The dimethylformamide (DMF) resonances illustrated this. Thirt labelled were employed in these examples substrates in this work, and this has two main effects upon the spectra. Use of these types of labeled substances enhance the detectability of these substances at low concentration. Thus, only labelled compounds, the substrate and products derived from it, are seen. (An exception is DMF when it is used as solvent for the substrate.) Because the substrates each contain two labelled carbons, there is another unique feature to these spectra. The resonance of each carbon is affected (split) by its adjoining $^{13}$C neighbor such that it appears as a doublet. Thus, in this work all doublets represent two carbon specie derived from the substrate.

The single carbom metabolites (carbon monoxide, bicarbonate, formate, cyanide) appear as singlets. The low concentrations employed still require a relatively high number of acquisitions to increase the signal to noise ratio in the final spectrum. An excellent introduction to $^{13}$C nmr and spectral analysis (12) is available.

The $^{13}$C nmr spectra were obtained with a General Electric QE-300 nmr spectrometer in the manner previously described. Generally an overnight (16 hr) acquisition was employed (8,11,13).

Kinetics. For the organic halides, chloride ion release rates were monitored by direct potentiometry as previously described (8,11,13)

EXAMPLE I—KINETiCS

Figure 1:
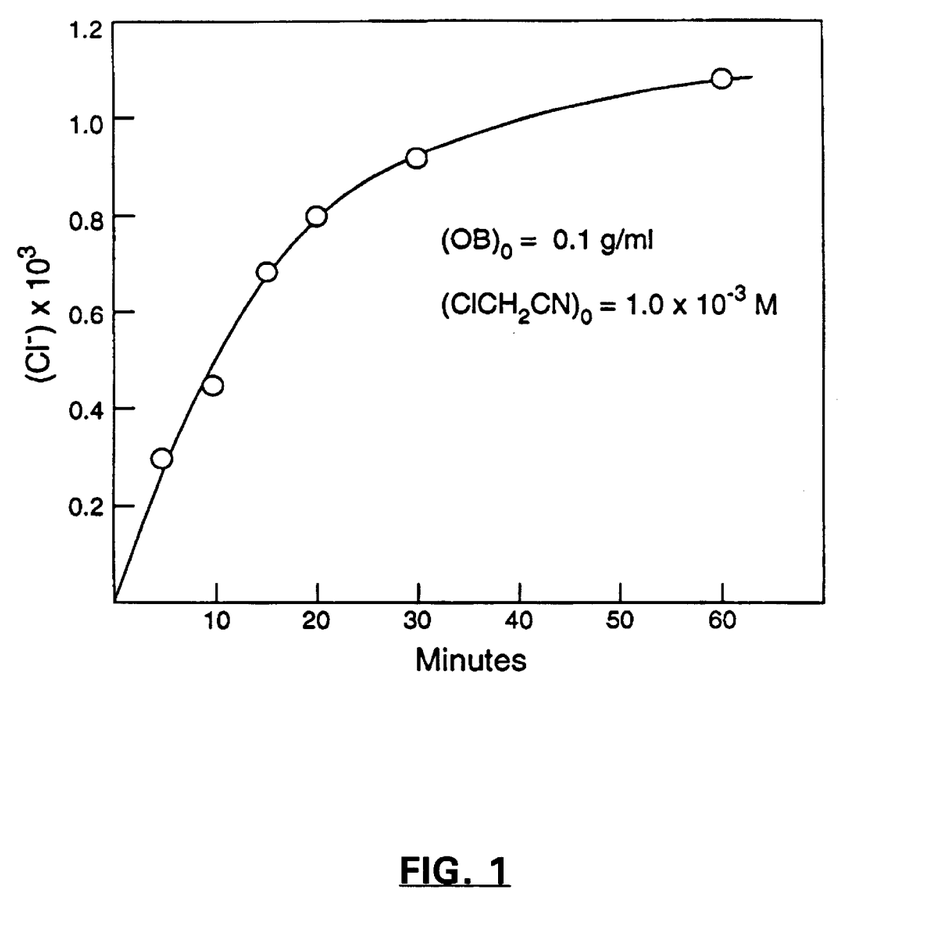
FIG. 1 Time course for chloride ion release from chloroecetonitrile by *Methylosinus trichosponrium*-OB-3b, pH 7,4, 0.1 M phosphate buffer.
Figure 2:
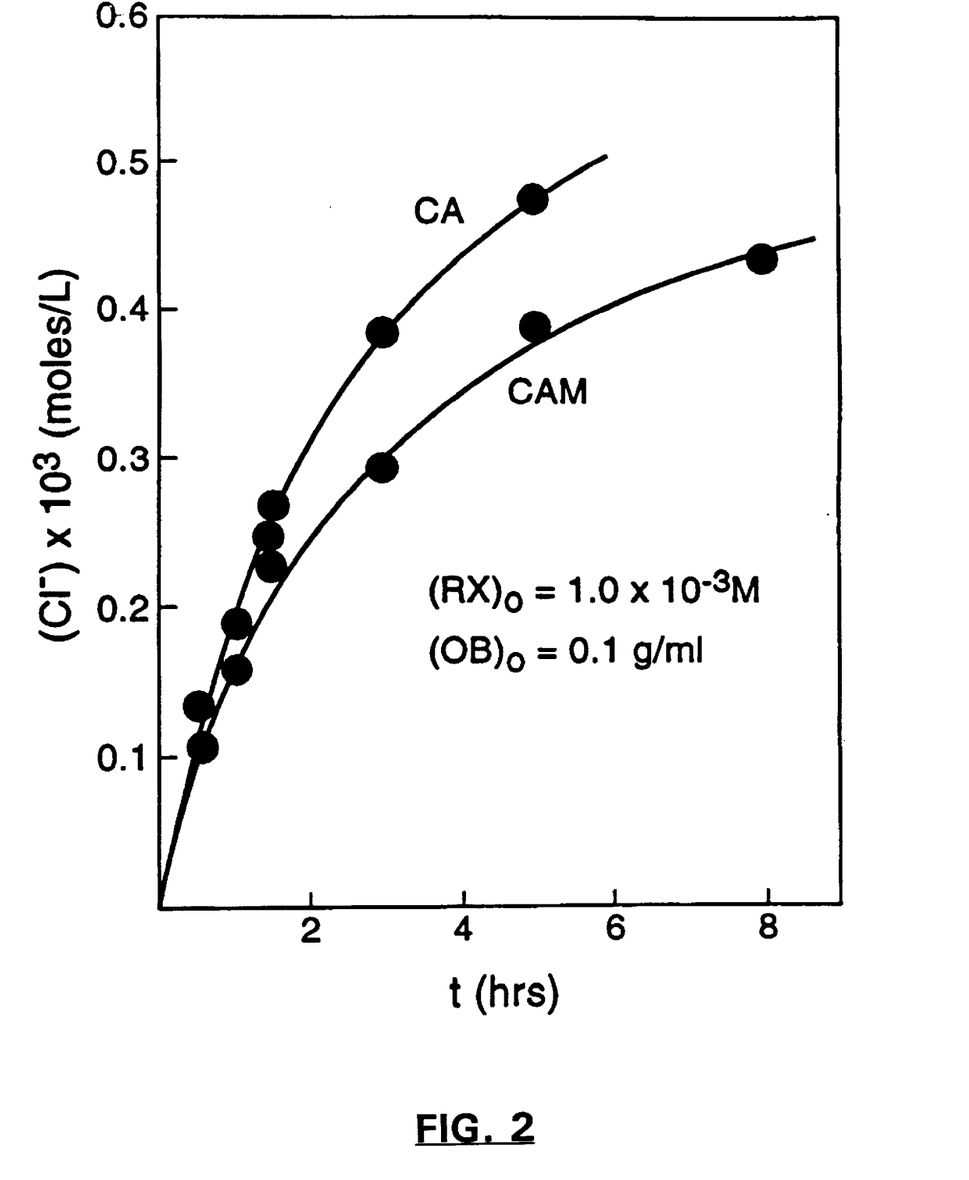
FIG. 2 Time course for chloride ion release from chloroacetamide (CAM) and chloroacetic acid (CA) by *Methylosinus trichosporium*-OB-3b, pH 7.4, 0.1 M phosphate buffer.

The rate of chloride ion release from chloroacetonitrile (CCN) by M. trichosporium OB-Δwas examined in the present study (see FIG. 1). As with the polyhalomethanes (8), the rate of conversion fell off sharply after the cells were held for one week. The half life at this cell density, estimated from initial slopes is 11 mins. This is very close to that observed for the methyl halides under these conditions (8). The corresponing amide chloroacetamide (CAM) and chloroacetic acid (CA) under identical conditions are slow to react and reactions often do not go to completion (FIG. 2). Half lives estimated from initial slopes for these latter are ~3.4 hrs.

CA had been observed to be inert or slow to react with this organism. It is the end metabolite from the partial conversion of ethylene dichloride by this organism (13). The kinetics for acetonitrile and cyanide transformations were not monitored, but some idea of the conversions can be obtained from the nmr data presented below. Cyanide ion is completely consumed in 24 hours. Acetonitrile is more than 62% converted to the cyanohydrin in 0.5 hours.

EXAPLELE II—REACTION PATHWAYS

The NMR analyte contains the entire incubation mixture. All $^{13}$C labelled substrates are observed directly and there is no doubt they are products derived from the parent substrate.

The $^{13}$C NMR spectrum of the acetonitrile incubation at 0.5 hrs was assessed.

The resonances for staring nitrile are at 28 (CH3) and 1188 (CN). The peak at 112.5 is a machine center spike. Clearly a large new resonance is observed at 476 and close examination of the nitrile resonance at 118 indicates an overlay of two doublets so that the 476 doublet is also coupled to it.

At 24 hrs, the methyl doublet for acetonitrile is nearly gone. The 478 doublet has increased and a new singlet at 1726 corresponding to formic acid has appeared. The overlap of the nitrile doublets in the CN range (~1186) is clearer in this spectrum. The unknown doublet at 476 was deduced to result from the cyanohydrin of formaldehyde. This was established by synthesizing the cyanohydrinn situ via the reaction of excess fonfalin with potassium cyanide in water.

EXAMPLE IV—CHLOROACETONITRILE

Chloroacetonitrile (CCN) is a more complicated substrate and the associated $^{13}$C nmr spectra taken at 5, 15, and 30 mins, and 24 hrs. For this substance, as well as CAM and CA substrates, the incubations were begun by injecting the cell suspension with the requisite amount of a 1 M solution of the substrate in dimethyl formamide (DMF). The DMF resonances appear as singlets at 165, 38, and 32d in the spectra. The 5 min spectrum, in addition to CCN (ClCH$_2$ at 25d, d and CN at 117d, d), exhibits a small but clear doublet at 17d along with two singlets corresponding to formate (172d) and cyanide (164d). At 15 min the 17d, d resonance is barely discernible. Cyanide and formate have increased. At 30 min, formate is the dominant product, but cyanide and traces of bicarbonate (161d can be seen. At 24 hrs, carbon monoxide (182d), formate, cyanide, and bicarbonate reonanc, along with carbon dioxide (123d) are visible. In addition, in the DMF methyl region, there are three new singlets at 33d, 35d, and 23d. These are unassigned and we presume they may represent utiliation of the CCN carbon source for the building of other cellular constituents containing $^{13}$C methyl moieties.

The initial reaction is not a direct microbiological hydroxylation of the C¾Cl bond. If this were to occur, the cyanohydrin of formaldehyde should be generated. It has a finite lifetime under these conditions as we have noted above, but no resonances in any of the spectra from CCN exhibits the 478, d (for HOCH2CN). Moreover, no resonance corresponding to chloroacetmide or chloroacetic acid are discernible. Thus, the CN moiety is not hydrolyzed in this case as it is not with acetonitrile. The initial doublet was assigned to the intermediate II (eqn 4). This, both halohydrin and cyanohydrin, would be expected to decompose by two pathways (4A and 4B). Path 4B with loss of HCN would generate formyl chloride. This substance is unstable and is established to decompose to formate by hydrolysis and CO by loss of HO (14). The same intermediate is inferred in the conversion of the methylene halides to CO and formate by this organism (8). Path (a), loss of HCl from II, would produce formyl nitrile. This substance is unknown. Like formyl chloride, the substance is expected to hydrolyze to formate and HCN or lose HCN to produce CO.

EXAMPLE V—CHLOROACETIC ACID

With chloroacetic acid, (CA), the 5 and 24 hr spectra are essentially the same. Both show a large amount of unracted CA (ClCH$_2$ 44d, d and CO$_2$H 176d, d). The hydrolysis product glycolic acid is observable (HOCH2 at 62d, d) as the first main product and a trace of 5 bicarbonate is observable. Thus, though poorly converted by OB-3b, the organism does directly hydrolyze the CCl bond of CA. Blank incubations with CA in buffer, but without cells, exhibit no hydrolysis in 2 weeks.

Like CA, chioroacetamide (CAM) undergoes a direct microbiological hydrolysis to hydroxyacetamide (HOCH2¾ at 626, d, ¾ CONH2 1804 361 d) though a greater conversion occurs with CAM than with CA (FIG. 5a). A greater conversion to bicarbonate is also apparent. An apparent 20% conversion to the hydroxy amide was evident in 3 hrs.

EXAMPLE VI—SOILS

Figure 3:
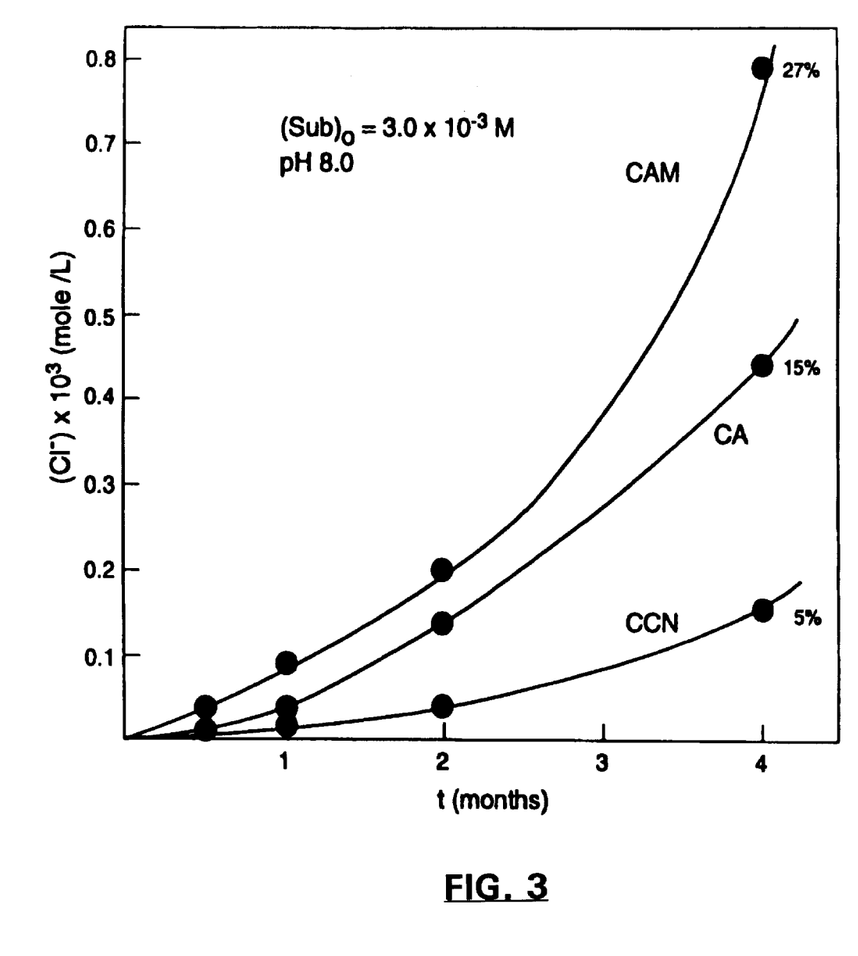
FIG. 3 Slow chloride ion release from chloroacetonitrile (CCN), chlororacetic acid (CA), and chloroactamide (CAM) at pH 8.0, phosphate buffer. The percent conversion at 4 mo is indicated.

The results with the dump soil site (Table 1) indicate a capacity for hydrolysis and oxidation. In addition, the results with CA alone indicate that this capacity is diminished upon storage for 1 year at 5° C. Thus, in contrast to the complete oxidation to HCO$_3$ observed in 2 weeks with the initial sample (d.S-1), no conversion at all was noted in the same period with the 1 year old sample. In contrast, the response of CAM and CCN to the 1 year old soil and a new fresh sample (d.S-2) was not markedly different. That is, both CAM and CCN were hydrolyzed to CA. Also with CCN, whether the incubation was aerobic or anaerobic did not make much difference. These results suggest that the hydrolysis of the amide and nitrile linkages with this soil may be chemical rather than microbiological in nature. Background rates for these conversions were separately assessed via NMR in phosphate buffer at pH 7.4. In 2 weeks, CAM hydrolyzed to CA to the extent of about 2%. CCN was inert. The background hydrolysis of the C—Cl bond of each of the probes was also assessed at 2 weeks and 1, 2, and 4 months at pH 6.0, pH 7.4, and pH 8.0. A plot for the data at pH 8.0 is shown in FIG. 5. The C—Cl bond hydrolysis is slow. Thus, only 5% of CCN had hydrolyzed to Cl in 4 months. The percent hydrolysis of CA and CAM in 4 months at pH 8.0 was 15 and 27% respectively. The results at 4 months at pH 7.4 [CCN (1%), CA (15%), CAM (21%)] and at pH [CCN (0), CA (2.5%), CAM (3%)] show the probe to be stable over the time period of the environmental incubations. Note at 2 weeks, pH 7.4, the maximum percent hydrolysis of the C—Cl bond was observed with CAM, and it was less than 1%.

EXAMPLE VII—ENVIROMENTAL SAMPLES

Soils. Two soil samples were employed. Both were taken from a dump site at UCR (d.S soil) that had been exposed to haloorganics and other pesticides for some time. The d.S-1 sample represents a homogenate of a 2-ft deep core taken from the center of the site. The d.S-2 sample was obtained from the edge of the site. A sample of d.S-1 was held for 1 year at 5° C. (d.S-1, 1-yr-old) to test any changes in reactivity upon storage.

Marine Coastal Water and Se&diments. These sea samples were taken from Shaw's Cove in Laguna Beach, Calif. Sea water was taken about 100 yards from shore at the surface. In addition, two samples of sediments were collected. The first, Shaw's Cover 1 (SC-1), was a grayish sandy sediment from the top 2 in. of the surface bottom at a depth of 30 ft. The second (SC-2) was a dark, near blackish silty sediment tamen at a depth of 40 ft from 3 to 5 in. below the surface bottom. These samples were slurries containing about a two-thirds liquid phase. Table 3 portrays the response of the probes to the coastal marine samples from Shaw's Cove.

Again the seawater itself was inactive toward CA, but the upper sandy sediment oxidized al three probes to HCO3-. With CCN, a hydrolysis of the nitrile moiety is also observed. The lower silty sediment incubated aerobically with CA exhibits a compete oxidation to bicarbonate. Incubated anaerobically, bicarbonate is still produced, but both hydrolysis and reduction products are detectable. CAM is oxidized aerobically, but mainly hydrolyzed to CA in the anaerobic incubation. CCN is both hydrolyzed to CA and oxidized. As with the Lake Perris sediments, these marine sediments exhibit a broad capacity for oxidation that may entail preliminary hydrolysis.

Lake Samples and Sediments. These were taken from Lake Perris, Riverside, Calif. Lake water (LPW) was a surface sample, and the sediments LP-1 and LP-2 represent an upper sandy sediment (top 1–2 in.) taken at a depth of 20 ft. and a lower black silty sand collected at 4–6 in. below the surface bottom at a depth of 12 ft. These slurries were about two-thirds liquid. Table 2 summarizes the responses of the probes to the ILake Perris samples upon aerobic and anaerobic (under H$_2$) incubations.

The surface water shows no conversion of CA in 2 weeks (ine 1). However, the upper sediment shows a rapid conversion of CA to bicarbonate (ine 2), and a sample incubated anaerobically shows no $^{13}C$ resonance at al at 1 week. CAM is partialy oxidized in both aerobic and anaerobic incubations and CCN is inert. The lower sediment exhibits about the same response to CA and CAM except that, in the anaerobic incubations, both the hydrolysis to CA and oxidation are observed. CCN, while not converted aerobically, is reduced to acetonitrile in the anaerobic incubaton. Thus, these sediments have the capacity for quick oxidation that may wel proceed via initial hydrolysis, and they have reductive capacity as well.

Acilvated Sludge. The sample of activated sludge (AS) was collected from the aeration tank at the Riverside City sewage plant. The blackish slurry contained about one-third solid by volume. The complete conversion of al of the probes in 2 weeks and less by the activated sludge sample is noted in Table 4.

Analyses. For soil, the following protocol was used: 1.0 g of sample was triturated with 2 mL of glass distilled water, and 2 µl of a 1 M $^{13}C$ probe in dimethylformamide (DMF) was added. The 30-mL volume test tube containing the reactants was capped with a serum cap, and samples were allowed to stand in a rack at room temperature. They were shaken once each day by hand. For anaerobic incubations (see below), the same procedure was employed except that the tube was gassed with hydrogen. At the desired time, approximately 1 mL (or al) of the slurry was centrifuged/filtered. The clear centrifugate (0.5–0.6 mL) was transferred to a serum capped NMR tube, and 100 µL of $D_2O$/mL of sample was added for the lock. Samples were held at 5° C. until the NMR acquisition could begin. The centrifuge filtration process required 10 min at 8000 rpm. It was accomplished with a microcentrifuge (Fisher Scientific). Small snap-cap plastic tbees (Eppendorf tubes) containing a 0.45-µm filter were convenient. Note: Unwashed plastic tubes from Rainin Instrument showed resonances at δ 63 and 73 in the filtrate. Tubes from Micron Supplies Incorporated did not.

Two mililiters of seawater and lake water as well as sediment and sludge slurries was incubated without dilution with 2 µL of a 1 M probe in DMF. The slurries were sle before removing the sample. The clear seawater and lake water samples required no centrifugation or filtration. The sediment slurries were centrifuged and filtered before NMR analysis as descnbed above for soil. For "anaerobic" incubations, unless otherwise stated, the tubes were gassed briefly (30 s) with hydrogen. As the results indicate, the samples were not completely anaerobic. This procedure allowed anaerobic transformations (reductions) to occur without completely suppressing oxidative reactions.

The NMR analysis was an overnight acquisition (16h) on a General Electric QE-300 spectrometer. The partial percent conversions were estimated from relative intensities of the α-carbon resonances except for $HCO_3^-$. This conversion was estated from the relative intensities of the $HCO_3^-$ resonances as compared to the C=O or C=N ronances of the starting probe or product. These latter are tertiary carbons and not subject to the NOE (nuclear Overhauser effect) enhancement attendant upon decoupling the proton resonances with irradiation (23). Hence, the corresponding resonances are less intense than those associated with the α-$CH_2X$ (X=Cl, OH) carbons. Based upon the close similarity of authentic spectra of the probes taken under the conditions described, the inherent intensities of these α-carbons were taken as the same for the purpose of estimating product distribution. Similarly, and upon the same basis, all tertiary carbons are taken as having the same (lesser) intensity in any given sample. Thus, percent conversions were deeeine on this basis. In samples where both the tertary and α-carbons were discernible, relative distributions calculated using either set of carbon intensities were the same(±5). The reproducibility of the distributions obtained from replicate samples for any analysis was within 10% of the values reported. This analysis assumes that al $^{13}C$-labeled carbons are equally visible in the centrifugate (no selective adsorption to the environmental matrix) and that the distribution of products observed is the true distribution. These highly water-soluble probes and products have large distribution coefficients such that their presence in water is greatly favored at $10^{-3}$ M. The spect of the probes and $^{13}C$-labeled bicarbonate exposed to the approximate 2:1 water/samples, where no reaction was detected, exhibited the same NMR spectrum (following centrifugation/filtration) as authentic standards at that concentration. Spectra are refined by the addition of acid. This result, in part, reflects the desorption of anions from the solid matrices.

Chloride analysis was accomplished by direct potentiometry at high ionic strength employing an Orion chloride ion electrode and a Calomel double-jacketed reference electrode as previously described (24).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, met and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

TABLE I

The response of Probes to Fresh and One Year Old[a] Dump Site Soil from UCR

| Environment | Probe | Time (wks) Incubation | Products | % Conversion[a] | Conclusion |
| --- | --- | --- | --- | --- | --- |
| d.S soil-1 (fresh) | CA | 2/anaerobic[e] sterilized | None | 0 | NRc, d |
| d.S soil-1 (fresh) | CA | 3/adj to pH 10 | $HOCH_2CO_2H$ | 80% | hydrolysisd |
| d.S soil-1 (fresh) | CA | 0.7/aerobic | $HCO_3^-$ | 33% | partial oxidation |
| d.S soil-1 (fresh) | CA | 2/aerobic | $HCO_3^-$-only | 100% | complete oxidations |

TABLE I-continued

The response of Probes to Fresh and One Year Old[a] Dump Site Soil from UCR

| Environment | Probe | Time (wks) Incubation | Products | % Conversion[a] | Conclusion |
|---|---|---|---|---|---|
| d.S soil-1 (fresh) | CA | 1/anaerobic[e] | HOCH$_2$CO$_2$H | 8% | hydrolysis |
| d.S soil-1 (1 year old) | CA | 2/aerobic | None | 0% | NR |
| d.S soil-1 (1 year old) | CAM | 2/aerobic | CA HCO$_3$- | 84% | amide hydrolysis (15) oxidation (69) |
| d.S soil-1 (1 year old) | CCN | 2/aerobic | CA | 50% | hydrolysis of CN |
| d.S soil-2 (fresh) | CA | 2/aerobic | HCO$_3$- | 100% | oxidation |
| d.S soil-2 (fresh) | CA | 2/anaerobic | HCO3-45% | | oxidation |
| d.S soil-2 (fresh) | CAM | 2/aerobic | CA HCO:F | 62% | amide hydrolysis (54) oxidation (8) |
| d.S soil-2 (fresh) | CAM | 2/anaerobic[f] | CA HCO$_3$- | 48% | amide hydrolysis (42) oxidation (6) |
| d.S soil-2 (fresh) | CCN | 2/aerobic | CA | 30% | hydrolysis of CN |
| d.S soil-2 (fresh) | CCN | 2/anaerobic[f] | CA | 30% | hydrolysis of CN |

[a]Stored at 5° C. for 1 yr; [b]estimated from $^{13}$C intensities; [c]NR = no reaction, probe recovered; [d]spectra given in ref. 5; [e]under argon; [f]under hydrogen

TABLE II

The response of Probes to Lake Perris Sediments

| Environment | Probe | Time (wks) Incubation | Products | % Conversion[a] | Conclusion |
|---|---|---|---|---|---|
| Surface water (LSW) | CA | 2/aerobic | None | 0% | NRb |
| LP-1 (upper sandy sediment) | CA | 1/aerobic | HCO$_3$- | 100% | complete oxidation |
| LP-1 (upper sandy sediment) | CA | 1/anaerobic[c] | od | 100% | all metabolized |
| LP-1 (upper sandy sediment) | CAM | 2/aerobic | HCO3- | 60% | oxidation |
| LP-1 (upper sandy sediment) | CAM | 2/anaerobicc | HCO3- | 30% | oxidation |
| LP-1 (upper sandy sediment) | CCN | 2/aerobic | None | 0% | NR |
| LP-1 (upper sandy sediment) | CCN | 2/anaerobicc | None | 0% | NR |
| LP-2 (lower silty sediment) | CA | 1/aerobic | HCO$_3$- only | 100% | complete oxidation |
| LP-2 (lower silty sediment) | CA | 2/aerobic | 0[d] | 100% | all metabolized |
| LP-2 (lower silty sediment) | CAM | 2/aerobic | HCO3- | 50% | oxidation |
| LP-2 (lower silty sediment) | CAM | 2/anaerobic[c] | CA HCO3- | 38% | amide hydrolysis (18) oxidation (20) |
| LP-2 (lower silty sediment) | CCN | 2/aerobic | None | 0% | NR |
| LP-2 (lower silty sediment) | CCN | 2/anaerobic | CH$_3$CN | 14% | reduction |

[a]estimated from $^{13}$C intensities; [b]NR = no reaction, probe recovered; [c]under H$_2$; [d]0 = no $^{13}$C resonances detected

TABLE III

The response of Probes to Marine Coastal Sediments[a]

| Environment | Probe | Time (wks) Incubation | Products | % Conversion[a] | Conclusion |
|---|---|---|---|---|---|
| Surface water (MSW) | CA | 5/aerobic | None | 0% | NR[c] |
| SC-1 (upper sandy sediment) | CA | 2/aerobic | $HCO_3-$ | 50% | oxidation |
| SC-1 (upper sandy sediment) | CA | 5/aerobic | $HCO_3-$ only | 100% | complete oxidation |
| SC-1 (upper sandy sediment) | CAM | 2/aerobic | $HCO_3-$ only | 100% | complete oxidation |
| SC-1 (upper sandy sediment) | CCN | 2/aerobic | CA $HCO_3-$ | 55% | hydrolysis of CN (11) oxidation (44) |
| SC-2 (lower silty sand sediment) | CA | 4/aerobic | $HCO_3-$ only | 100% | complete oxidation |
| SC-2 (lower silty sand sediment) | CA | 4/anaerobic[d] | $CH_3CO_2H$ $HOCH_2COH$ $HCO_37$ | 57% | reducation (1) hydrolysis (6) oxidation (50) |
| SC-2 (lower silty sand sediment) | CAM | 2/aerobic | $HCO_3-$ only | 100% | complete oxidation |
| SC-2 (lower silty sand sediment) | CAM | 2/anaerobic[d] | CA $HCO3-$ | 68% | amide hydrolysis (25) oxidation (43) |
| SC-2 (lower silty sand sediment) | CCN | 2/aerobic | $HCO_3-$ | 50% | oxidation |

[a]from Shaw's Cove, Laguna Beach, CA; [b]estimated from $^{13}C$ intensities; [c]NR = no reaction, probe recovered; [d]under H2

TABLE IV

The response of Probes to Activated Sludge

| Environment | Probe | Time (wks) Incubation | Products | % Conversion[a] | Conclusion |
|---|---|---|---|---|---|
| Activated Sludge (AS) | CA | 0.57/aerobic | $HCO_3-$ | 50% | oxidation |
| Activated Sludge (AS) | CA | 2/aerobic | $HCO_37$ | 100% | complete oxidation |
| Activated Sludge (AS) | CA | 2/anaerobic | $HOCH_2COH$ $HCO3-$ | | 87% hydrolysis (33) oxidation (54) |
| Activated Sludge (AS) | CAM | 0.71/aerobic | CA $HCO_3-$ | 100% | amide hydrolysis (35) oxidation (65) |
| Activated Sludge (AS) | CAM | 2/aerobic | $HCO_3-$ Only | 100% | oxidation |
| Activated Sludge (AS) | CAM | 0.86 anaerobic | CA $HCO_3-$ | 100% | amide hydrolysis (60) oxidation (40) |
| | CAM | 2/anaerobic | CA $HCO_3-$ | 100% | amide hydrolysis (40) oxidation (60) |
| | CCN | 0.71/aerobic | CA $HCO_3-$ | 100% | CN hydrolysis (65) oxidation (40) |
| | CCN | 2/aerobic | $HCO_3-$ | 100% | oxidation |
| | CCN | 2/anaerobic | CA $HOCH_2COH$ $HCO_3-$ | 100% | hydrolysis: alide (55) C-Cl (15) oxidation (35) | a estimated from $^{13}C$ intensities

REFERENCES (1) *Merck Index*, 10th ea.; Windholtz, E.; Budavari; S., Blumett, R F.; Otterbein, E. S.; Eds.; Merck & Co., Rahway, New Jersey, 1983.
(2) Ahmed, A. E.; Farooqui, M. Y. H.; Trieff, N. M. Nitriles; *Bioactivation of Foreign Compounds*; Anders, M. W. Ed.; Academic: New York, Chapter 17, pp 485 518.
(3) Firmin, J. L.; Gray, D. O. *Biochem. J.* 1976,158, 223–229.
(4) Nishiyama, M.; Horinouchi, S.; Kobyashi, M.; Nagasawa, T.; Kamada, H.; Beppu, T. *J. Bact.* 1991, 173, 2465–2472.
(5) Lang, S. *Arch. Exp. Pathol. Phaimkol.* 1894, 34, 247–248.
(6) Fox, B. G.; Froland, W. A.; Jollie, D. R.; Lipscomb, J. D. *Methods in Enzymology*; lidstrom, M. E., Ed.; Academic: New York, 1990, Vol. 188, pp 191–202.
(7) Green, J.; Dalton, H. J. *Biol. Chem.* 1989, 264, 17698–17703.
(8) Bartnicki, E. W.; Castro, C. E. *Environ. Toxicol. Chem.* 1994, 13, 241–245.
(9) Castro, C. E.; O'Shea, S. K.; Wang, W.; Bartnicld, E. W. *Environ Sci. Technol.* 1995 (submitted for publication).
(10) Castro, C. E.; O'Shea, S. K.; Bartnicki, E. W. *Environ. Sci. Technol.* 1995 (in press).
(11) Riebeth, D. M.; Belser, N. O.; Castro, C. E. *Environ. Toxicol. Chem.* 1992,11, 497501.
(12) Silverstein, R M.; Bassler, G. C.; Morrill, T. C. *Spectrometric Identification of Organic Conpounds*; John Wiley & Sons, N. Y. 1981
(13) Castro, C. E.; Riebeth, D. M.; Belser, N. O. *Environ. Toxicol. Chem.* 1992,11, 749755.
(14) Krauskopf, K. B.; Rollefson, G. K. *J. Am. Chem. Soc.* 1934, 56, 2542–2548.
(15) Castro, C. E. *Environ. Toxicol. Chem.* 1993, 12, 1609–1618.
(16) Riebeth, D. M.; Belser, N. O.; Castro, C. E. *Environ. Toxicol. Chem.* 1992, 11, 497–501.
(17) Castro, C. E.; Riebeth, D. M.; Belser, N. O. *Environ. Toricol. Chem.* 1992, 11 749–755.
(18) Castro, C. E.; Wade, R. S., Riebeth, D. M.; Bartnicki, E. W.; Reiser, N. O. *Environ. Toxicol. Chem.* 1992, 11, 757–764.
(19) Bartiicki, E. W.; Castro, C. E.; *Environ. Toxicol. Chem.* 1994, 13, 241–245.
(20) Castro, C. E.; O'Shea, S. K.; Bartiicki, E. W.; *Environ. Toxicol Chem.* 1995, 29, 2154–2156.
(21) Castro, C. E.; O'Shea, S. K.; Wang, W.; Bartnicki, E. W., *Environ. Sci. Technol.* 1996, 30, 1180–1184.
(22) Finan, P. A.; Fathergill, G. A.; *J. Chem. Soc.* 1992, 2824–2825.
(23) Silverstein, R. M.; Bassler, G. C.; Morril, T. C. *Spectrometric Identification of Organic Conpounds*, 4th ed.; John Wiley and Sons: New York, 1981: Chapter 5, pp 249–303.
(24) Belser, N O.; Castro, C. E.; *J. Agric. Food Chem.* 1971, 19, 22–26.
(25) Klump, G. *Reactivity in Organic Chemistry*, John Wiley and Sons: New York, 1982.
(26) Castro, C. E. *Environ. Toxicol. Chem.* 1993, 12, 1609–1618.

What is claimed is:

1. An environmental assessment system for a method of assessing an oxidative, reductive, or substitution reactivity of a tested environmental region, said system consisting essentially of:

a) a sample in aqueous solution or suspension obtained from the tested environmental region;

b) a water soluble environmental chemical probe capable of undergoing reduction, oxidation or substitution selected from the group consisting of 1,2-$^{13}$C-chloroacetic acid, 1,2-$^{13}$C-chloroacetamide or 1,2-$^{13}$C-chloroacetonitrile;

c) an incubation container for incubating the sample with the probe;

d) nuclear magnetic resonance spectrometer for determination of a relative distribution of an oxidative, reductive or substitutive conversion product and an unreacted probe; and e) means for calculating a percentage of conversion of the environmental probe into an oxidative, reductive or substitutive product following the incubation of the sample with the probe and utilizing said percentage of conversion as a measure of the environmental region reactivity.

2. The system of claim 1 wherein the probe is 1,2-$^{13}$C-chloroacetic acid.

3. The system of claim 1 wherein the environmental sample is a soil sample, a fresh or marine water sample, a fresh or marine water sediment sample, a land fill sample, a sewage sample, a biological product, seed, grain or a plant sample.

4. A kit for assessment and monitoring of reactivity potential of an environmental region by detecting chemical or biological transformation of a chemical environmental probe, said kit consisting essentially of:

the means for collecting an environmental sample of the tested environmental region;

a chemical environmental probe selected from the group consisting of 1,2-$^{13}$C-chloroacetic acid, 1,2-$^{13}$C-chloroacetamide or 1,2-$^{13}$C-chloroacetonitrile, said probe capable of undergoing reduction, oxidation or substitution in response to chemical or biological transformation;

a means for contacting said sample with said chemical probe;

a means for incubating said sample contacted with said chemical probe;

a means for detecting the presence, absence and degree of the reactivity of the tested environmental region by detecting a percentage of an oxidative, reductive, or substitutive product in said sample contacted and incubated with said probe;

a means for calculating the percentage of the conversion of the unreacted probe into the reaction product; and a means for correlating said percentage of the conversion to the reactivity potential of the tested environmental region.

5. The kit of claim 4 wherein the environmental probe is 1,2-$^{13}$C-chloroacetic acid.

6. The kit of claim 4 wherein the environmental probe in 1,2-$^{13}$C-chloroacetamide.

7. The kit of claim 4 wherein the environmental probe is 1,2-$^{13}$C-chloroacetonitrile.

8. A method for assessment and monitoring of the reactivity potential of an environmental region by detecting chemical or biological transformations of a chemical environmental probe, said method comprising steps:

(a) collecting an environmental sample of the tested environmental region;

(b) contacting said sample with the chemical environmental probe selected from the group consisting of 1,2-$^{13}$C-chloroacetic acid, 1,2-$^{13}$C-chloroacetamide or 1,2-

$^{13}$C-chloroacetonitrile, wherein said probe is capable of undergoing reduction, oxidation or substitution in response to chemical or biological transformation;

(c) incubating said sample contacted with the chemical probe;

(d) detecting the presence, absence and degree of reactivity of the tested environmental region by determining a percentage of an oxidative, reductive, or substitutive product in said sample contacted and incubated with said probe;

(e) calculating the percentage of the conversion of the unreacted probe into the reaction product; and (f) correlating said percentage to an environmental region reactivity potential.

9. The method of claim 8 wherein the sample and the probe in an aqueous mixture are incubated for 1 to 2 weeks.

10. The method of claim 9 for assessment of substitutive reactivity of the tested environmental region.

11. The method of claim 8 wherein the presence or absence of reactivity in determined from the percentage of conversion of the oxidative, reductive or substitutive product and the unreacted probe following incubation of a reaction mixture containing said sample and said probe.

12. The method of claim 11 wherein the environmental region has a high reactivity if the conversion of the probe to the oxidative, reductive, or substitutive product is between 50–100% and a low reactivity if the conversion of the probe is between 0–10%.

13. The method of claim 8 wherein the environmental sample is a soil sample, a fresh or marine water sample, a fresh or marine water sediment sample, a land fill sample, a sewage sample, a biological product, seed, grain or a plant sample.

14. The method of claim 13 wherein the presence or absence of reactivity is determined from the percentage of conversion of the probe to oxidative, reductive or substitutive product following incubation of a reaction mixture containing said sample and said probe.

15. The method of claim 14 wherein the environmental region has a high reactivity if the conversion of the probe to the oxidative, reductive, or substitutive product is between 50–100% in two weeks and a low reactivity if the conversion of the probe is between 0–10% in a month.

16. The method of claim 15 wherein the environmental probe of step (b) is 1,2-$^{13}$C-chloroacetic acid.

17. The method of claim 15 wherein the environmental probe of step (b) is 1,2-$^{13}$C-chloroacetamide.

18. The method of claim 15 wherein the environmental probe of step (b) is 1,2-$^{13}$C-chloroacetonitrile.

* * * * *

UNITED STATES PATENT AND TRADEMARK OFFICE
CERTIFICATE OF CORRECTION

PATENT NO. : 6,030,843
DATED : February 29, 2000
INVENTOR(S) : Charles E. Castro It is certified that error appears in the above-identified patent and that said Letters Patent is hereby corrected as shown below:

ABSTRACT,
Line 1, delete "136" and insert -- 13C-labeled --;
Line 2, delete "chloroactonitrile" and insert -- chloroacetonitrile --;
Line 6, delete "marne" and insert -- marine --;

Column 1,
Line 64, delete "13X13CHR$_1$-Y" and insert -- X-13CHR$_1$-Y --;

Column 2,
Line 38, delete "10-9" and insert -- $10^{-9}$ --;
Line 44, delete "10-3" and insert -- $10^{-3}$ -- ;

Column 3,
Line 12, delete "clement" and insert -- element --;
Line 24, delete *"trichosponrium"* and insert -- trichosporium --;
Line 31, delete "chloroactamide" and insert -- chloroacetamide --;
Line 41, delete "25";
Line 42, delete "-";
Line 50, delete "CaCl$^2$" and insert -- CaCl$_2$ --;
Line 52, delete "Pcl$_8$" and insert -- PCl$_5$ --;
Line 59, delete "C." and insert -- C --;
Line 63, delete "unread" and insert -- unreacted --;
Line 64, delete "C." and insert -- C --;
Line 66, delete "C." and insert -- C --;

UNITED STATES PATENT AND TRADEMARK OFFICE
CERTIFICATE OF CORRECTION

PATENT NO. : 6,030,843
DATED : February 29, 2000
INVENTOR(S) : Charles E. Castro It is certified that error appears in the above-identified patent and that said Letters Patent is hereby corrected as shown below:

Column 4,
Line 8, delete "C." and insert -- C --;
Line 13, delete "C." and insert -- C --;
Line 16, delete "C." and insert -- C --;
Line 17, delete "concentratedammonium" and insert -- concentrated ammonium --;
Line 31, delete "C." and insert -- C --;
Line 34, delete "sting" and insert -- stirring --;
Line 35, delete "C." and insert -- C --;
Line 37, delete "$^{13}$c" and insert -- $^{13}$C --;
Line 42, delete "manne" and insert -- marine --;
Line 44, delete "an" and insert -- all --;
Line 65, delete "nitrire" and insert -- nitrile --;

Column 5,
Line 24, delete "mineral on if" and insert -- mineralization is --;
Line 43, delete "C." and insert -- C --;
Line 64, delete "pl" and insert -- $\mu$l --;

Column 6,
Line 4, delete "Thirt" and insert -- Thirteen --;
Line 4, insert -- substrates -- after "labelled";
Line 4, insert -- , -- after "examples";
Line 5, delete "substrates in this work";
Line 16, delete "carbom" and insert -- carbon --;
Line 31, delete "KINETiCS" and insert -- KINETICS --;
Line 33, delete "M. trichosporium OB-$\delta$" and insert -- M. *trichosporium* OB-3b --;
Line 53, delete "EXAPLELE" and insert -- EXAMPLE --;
Line 60, delete "staring" and insert -- starting --;
Line 60, delete "28" and insert -- 2$\delta$ --;
Line 61, delete "1188" and insert -- 118$\delta$ --;
Line 62, delete "476" and insert -- 47$\delta$ --;
Line 64, delete "476" and insert -- 47$\delta$ --;
Line 67, delete "478" and insert -- 47$\delta$ --;

UNITED STATES PATENT AND TRADEMARK OFFICE
CERTIFICATE OF CORRECTION

PATENT NO. : 6,030,843
DATED : February 29, 2000
INVENTOR(S) : Charles E. Castro It is certified that error appears in the above-identified patent and that said Letters Patent is hereby corrected as shown below:

Column 7,
Line 1, delete "1726" and insert -- 172δ --;
Line 2, delete "1186" and insert -- 118δ --;
Line 3, delete "476" and insert -- 47δ --;
Line 5, delete "cyanohydrinn" and insert -- cyanohydrin in --;
Line 6, delete "fonfalin" and insert -- formalin --;
Line 10, insert -- were -- after "spectra";
Line 14, delete "165 38 and 32d", and insert -- δ165, 38, and 32 --;
Line 15, delete "25d, d" and insert -- δ25 d --;
Line 16, delete "117d, d" and insert -- δ117 d --;
Line 16, delete "17d" and insert -- δ17 d --;
Line 17, delete "172d" and insert -- 172δ --;
Line 18, delete "164d" and insert -- 164δ --;
Line 18, delete "17d,d" and insert -- δ17 d --;
Line 21, delete "161d" and insert -- 161δ --;
Line 22, delete "182d" and insert -- 182δ --;
Line 23, delete "123d" and insert -- 123δ --;
Line 24, delete "33d, 35d" and insert -- 33δ, 35δ --;
Line 25, delete "23d" and insert -- 23δ --;
Line 30, delete "C¾C1" and insert -- C-Cl --;
Line 35, delete "chloroacetmide" and insert -- chloroacetamide --;
Line 40, delete "(4A and 4B)";
Line 51, delete "unracted" and insert -- unreacted --;
Line 52, delete "44d" and insert with -- 44δ --;
Line 52, delete "176d" and insert --176δ --;
Line 53, delete "HOCH2 at 62d" and insert -- HOCH$_2$ at 62δ --;
Line 55, delete "5";
Line 59, delete "chioroacetamide" and insert -- chloroacetamide --;
Line 60, delete "¾";
Line 61, delete "626" and insert -- 62δ --;
Line 61, delete "¾";
Line 61, delete "1804 361" and insert -- at δ180,d --;
Line 62, delete "(FIG. 5a)"

UNITED STATES PATENT AND TRADEMARK OFFICE
CERTIFICATE OF CORRECTION

PATENT NO. : 6,030,843
DATED : February 29, 2000
INVENTOR(S) : Charles E. Castro It is certified that error appears in the above-identified patent and that said Letters Patent is hereby corrected as shown below:

Column 8,
Line 19, delete "FIG. 5" and insert -- Fig.3 --;
Line 36, delete "C." and insert -- C --;
Line 38, delete Se&diments" and insert -- Sediments --;
Line 49, delete "al" and insert -- all --;
Line 66, delete "Ilake" and insert -- Lake --;

Column 9,
Line 2, delete "ine 1" and insert -- line 1 --;
Line 3, delete "ine 2" and insert -- line 2 --;
Line 4, delete "at al at" and insert -- at all at --;
Line 10, delete "incubaton" and insert -- incubation --;
Line 12, delete "wel" and insert -- well --;
Line 14, delete "Acilvated" and insert -- Activated --;
Line 17, delete "of al of and insert -- of all of --;
Line 29, delete "(or al)" and insert -- (or all) --;
Line 32, delete "C." and insert -- C --;
Line 36, delete "tbees" and insert -- tubes --;
Line 43, delete "sle" and insert -- shaken --;
Line 47, delete "descnbed" and insert -- described --;

Column 10,
Line 3, delete "estated" and insert -- estimated --;
Line 4, delete "C=N ronances" and insert -- C≡N resonances --;
Line 17, delete "deeeine" and insert -- determined --;
Line 22, delete "al" and insert -- all --;
Line 28, delete "spect" and insert -- spectra --;
Line 45, delete "met" and insert -- methods --;
Table I, fifth column, delete "hydrolysisd" and insert -- hydrolysis --;

Column 11,
Table II, fourth column "Products", line 3, delete "od" and insert -- $O^d$ --.

UNITED STATES PATENT AND TRADEMARK OFFICE
CERTIFICATE OF CORRECTION

PATENT NO.   : 6,030,843
DATED        : February 29, 2000
INVENTOR(S)  : Charles E. Castro It is certified that error appears in the above-identified patent and that said Letters Patent is hereby corrected as shown below:

Column 13,
Table IV, fourth column, line 3, delete "HC037" and insert -- $HC0_3$ --; sixth column, line 18, delete "alide" and insert -- amide --;

Column 15,
Line 13, delete "Phaimkol." and insert -- Pharmakol --;
Line 16, delete "lidstrom" and insert -- Lidstrom --;
Line 23, delete "Environ Sci." and insert -- Environ. Sci. --;
Line 29, delete "Conpounds" and insert -- Compounds --;
Line 40, delete "Toricol." and insert -- Toxicol --;
Line 44, delete "Bartiicki" and insert -- Bartnicki --;
Line 46, delete "Bartiicki" and insert -- Bartnicki --;

Column 17,
Line 20, delete "reactivity in" and insert -- reactivity is --.

Signed and Sealed this

Twenty-fifth Day of December, 2001

*Attest:*

*Attesting Officer*

JAMES E. ROGAN
*Director of the United States Patent and Trademark Office*